United States Patent [19]

Audousset et al.

[11] Patent Number: 5,578,087
[45] Date of Patent: Nov. 26, 1996

[54] DYEING COMPOSITIONS FOR KERATINOUS FIBRES BASED ON PARA-PHENYLENE-DIAMINES, META-PHENYLENEDIAMINE AND BENZIMIDAZOLE DERIVATIVES, AND DYEING PROCESS EMPLOYING THEM

[75] Inventors: Marie P. Audousset, Levallois-Perret; Jean Cotteret, Verneuil-sur-Seine, both of France

[73] Assignee: L'Oreal, Paris, France

[21] Appl. No.: 461,844

[22] Filed: Jun. 5, 1995

Related U.S. Application Data

[63] Continuation of Ser. No. 174,009, Dec. 28, 1993, abandoned.

[30] Foreign Application Priority Data

Dec. 30, 1992 [FR] France .................... 92 15945

[51] Int. Cl.$^6$ .................................... A61K 7/13
[52] U.S. Cl. .................... 8/409; 8/406; 8/408; 8/410; 8/411; 8/412; 8/423
[58] Field of Search ................. 8/405, 406, 408, 8/409, 410, 411, 412, 423

[56] References Cited

U.S. PATENT DOCUMENTS

| | | | |
|---|---|---|---|
| 3,658,455 | 6/1969 | Kalopissis et al. | 8/409 |
| 5,203,875 | 4/1993 | Tuloup et al. | 8/405 |

FOREIGN PATENT DOCUMENTS

| | | |
|---|---|---|
| 0004368 | 10/1979 | European Pat. Off. . |
| 0467026 | 1/1992 | European Pat. Off. . |
| 1921911 | 2/1970 | Germany . |
| 2205111 | 11/1988 | United Kingdom . |

*Primary Examiner*—Paul Lieberman
*Assistant Examiner*—Caroline L. Dusheck
*Attorney, Agent, or Firm*—Jacobson, Price, Holman & Stern, PLLC

[57] ABSTRACT

Processes for the oxidative dyeing of keratinus fibers with compositions which comprise benzimidazole derivatives as couplers, at least one metaphenylenediaxnine and at least one para or ortho oxidation dye precursor, the benzimidazole derivative corresponding to the formula:

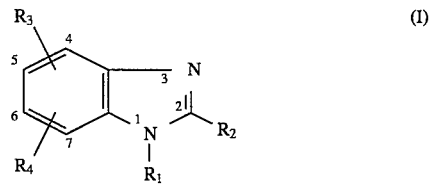

(I)

in which:

$R_1$ represents a hydrogen atom or a $C_1$–$C_4$ alkyl radical;

$R_2$ represents a hydrogen atom or a $C_1$–$C_4$ alkyl radical or a phenyl radical;

$R_3$ represents a hydroxyl, amino or methoxy radical;

$R_4$ represents a hydrogen atom or a hydroxyl or methoxy or $C_1$–$C_4$ alkyl radical;

with the proviso that:
when $R_3$ denotes $NH_2$, it occupies position 4;
when $R_3$ is at position 4, $R_4$ is at position 7;
when $R_3$ is at position 5, then $R_4$ is at position 6.

20 Claims, No Drawings

DYEING COMPOSITIONS FOR KERATINOUS FIBRES BASED ON PARA-PHENYLENE-DIAMINES, META-PHENYLENEDIAMINE AND BENZIMIDAZOLE DERIVATIVES, AND DYEING PROCESS EMPLOYING THEM

This is a continuation of application Ser. No. 08/174,009, filed Dec. 28, 1993, now abandoned.

The present invention relates to new dyeing compositions for keratinous fibres, and especially for human hair, containing oxidation dye precursors and couplers derived from benzimidazole and meta-phenylenediamines, and to dyeing processes employing such compositions.

It is known to dye keratinous fibres, and especially human hair, with dyeing compositions containing oxidation dye precursors, and especially para-phenylenediamines and ortho- or para-aminophenols generally known as "oxidation bases".

It is also known that the hues obtained with these oxidation bases may be varied by combining them with couplers also known as colour modifiers, chosen, in particular, from aromatic meta-diamines, meta-aminophenols and meta-diphenols.

Aromatic meta-diamines are known especially to enable blue or grey hues to be obtained with para-phenylenediamines.

French Patent FR-A-2,013,346 describes the use as coupler of benzimidazole derivatives enabling coloration ranges extending from blond to blue and grey to be obtained.

In German Patent DE-A-2,812,678, the use of other benzimidazole derivatives is also described, their dyeing properties being mentioned.

Oxidation dye precursors or couplers enabling a coloration having satisfactory resistance to light, washing, inclement weather and perspiration to be imparted to hair are sought in the hair dyeing field.

Concern is focused more especially on obtaining colorations which display very good behaviour in response to alternate irradiation and washing.

The abovementioned compositions of the prior art are not completely satisfactory from this standpoint, in particular as regards the production of ashen or blue hues.

The Applicant discovered, surprisingly, that the use of a coupler derived from benzimidazole combined with meta-phenylenediamines and with oxidation bases of the family of para and/or ortho derivatives led to colorations displaying especially noteworthy tenacity, in particular when the dyed keratinous fibres, and especially human hair, are subjected to alternate exposure to irradiation, in particular to UV rays, and to repeated washes.

The subject of the invention is hence dyeing compositions intended for use for the oxidation dyeing of keratinous fibres, and especially human hair, containing para and/or ortho type oxidation dye precursors and couplers consisting of at least one benzimidazole derivative and at least one meta-phenylenediamine.

The subject of the invention is also the use of benzimidazole as coupler in an oxidation dyeing composition containing a para and/or ortho oxidation dye precursor and a meta-phenylenediamine.

Another subject of the invention consists of the process for dyeing keratinous fibres, and especially human hair, employing such compositions in the presence of an oxidizing agent.

Other subjects of the invention will become apparent on reading the description and examples which follow.

The benzimidazole derivatives used as couplers for the oxidation dyeing of keratinous fibres, and especially human hair, in the presence of at least one meta-phenylenediamine and at least one para and/or ortho oxidation dye precursor, correspond to the formula (I):

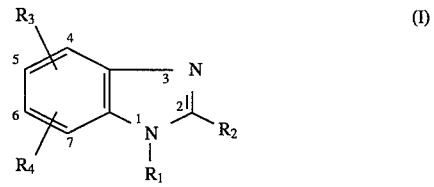

in which:

$R_1$ represents a hydrogen atom or a $C_1$–$C_4$ alkyl radical;

$R_2$ represents a hydrogen atom or a $C_1$–$C_4$ alkyl radical or a phenyl radical;

$R_3$ represents a hydroxyl, amino or methoxy radical;

$R_4$ represents a hydrogen atom or a hydroxyl or methoxy or $C_1$–$C_4$ alkyl radical;

with the proviso that:
when $R_3$ denotes $NH_2$, it occupies position 4;
when $R_3$ is at position 4, $R_4$ is at position 7;
when $R_3$ is at position 5, then $R_4$ is at position 6.

The benzimidazoles which can be used more especially are 4-hydroxybenzimidazole, 4-aminobenzimidazole, 4-hydroxy-7-methylbenzimidazole, 2-methyl-4-hydroxybenzimidazole, 1-butyl-4-hydroxybenzimidazole, 2-methyl-4-aminobenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole and 5,6-dimethoxybenzimidazole.

4-Hydroxybenzimidazole is more especially preferred.

The para or ortho type dye precursors are compounds which are not dyes in themselves, but which form a dye by a process of oxidative condensation, either with themselves or in the presence of a coupler or modifier.

These compounds contain functional groups, either two amino groups, or an amino group and a hydroxyl group, in the para or ortho position with respect to one another.

The para type oxidation dye precursors are chosen more especially from para-phenylenediamines, para-aminophenols, heterocyclic para precursors such as 2,5-diaminopyridine, 2-hydroxy-5-aminopyridine and tetraaminopyrimidine and so-called "double" bases of the bis(phenyl)alkylenediamine family.

As para-phenylenediamines, there may be mentioned the compounds corresponding to the formula (II) below:

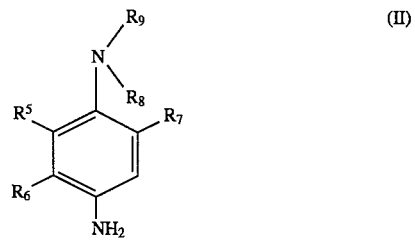

in which:

$R_5$, $R_6$ and $R_7$, which may be identical or different, represent a hydrogen or halogen atom, an alkyl or hydroxyalkyl radical having 1 to 4 carbon atoms, an alkoxy radical having 1 to 4 carbon atoms or a carboxyl or sulpho radical;

$R_8$ and $R_9$, which may be identical or different, represent a hydrogen atom or an alkyl, hydroxyalkyl, alkoxyalkyl, carbamoylalkyl, mesylaminoalkyl, acetylaminoalkyl, ureidoalkyl, carbalkoxyaminoalkyl, sulphoalkyl, piperidinoalkyl or morpholinoalkyl radical, these alkyl or alkoxy groups having from 1 to 4 carbon atoms, or alternatively $R_8$ and $R_9$, together with the nitrogen atom to which they are linked, form a piperidino or morpholino heterocycle, with the proviso that $R_5$ or $R_7$ represents a hydrogen atom when $R_8$ and $R_9$ do not represent a hydrogen atom, as well as the salts of these compounds.

Among the compounds of formula (II), there may be mentioned p-phenylenediamine, p-toluylenediamine, methoxy-para-phenylenediamine, chloro-para-phenylenediamine, 2,6-dimethyl-para-phenylenediamine, 2,6-diethyl-paraphenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-paraphenylenediamine, N,N-dipropyl-para-phenylenediamine, 3-methyl-4-amino-N,N-diethylaniline, N,N-bis (β-hydroxyethyl) -para-phenylenediamine, 3-methyl-4-amino-N,N-bis-(β-hydroxyethyl) aniline, 3-chloro-4-amino-N,N-bis-(β-hydroxyethyl) aniline, 4-amino-N-ethyl-N-(carbamoylmethyl)aniline, 3-methyl-4-amino-N-ethyl-N-(carbamoylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(4-acetylaminoethyl)aniline,4-amino-N-(β-methoxyethyl)aniline, 3-methyl-4-amino-N-ethyl-N-(β-acetylaminoethyl)aniline, 4-amino-N-ethyl-N-(β-mesylaminoethyl) aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine, N-(4-aminophenyl)piperidine, 2-hydroxyethyl-para-phenylenediamine, fluoro-para-phenylenediamine, carboxy-para-phenylenediamine, sulpho-para-phenylenediamine, 2-isopropyl-paraphenylenediamine, 2-n-propyl-para-phenylenediamine, hydroxy-2-n-propyl-para-phenylenediamine and 2-hydroxy-methyl-para-phenylenediamine.

These para type oxidation dye precursors may be introduced into the dyeing composition either in free base form, or in the form of salts, such as in hydrochloride, hydrobromide or sulphate form.

Among p-aminophenols, there may be mentioned p-aminophenol, 2-methyl-4-aminophenol, 2-chloro-4-aminophenol, 3-chloro-4-aminophenol, 2,6-dimethyl-4-aminophenol, 3,5-dimethyl -4-aminophenol, 2,3-dimethyl-4-aminophenol, 2-hydroxymethyl -4-aminophenol, 2-(β-hydroxyethyl)-4-aminophenol, 2-methoxy-4-aminophenol, 3-methoxy-4-aminophenol, 2,5-dimethyl-4-aminophenol, 2-methoxy-methyl-4- aminophenol, 2-aminomethyl-4-aminophenol and 2-(β-hydroxyethylaminomethyl)-4-aminophenol.

The ortho type oxidation dye precursors are chosen from ortho-aminophenols such as 1-amino-2-hydroxybenzene, 6-methyl-1-hydroxy-2-aminobenzene, 4-methyl-1-amino-2-hydroxybenzene and ortho-phenylenediamines.

The so-called double bases are bis(phenyl)-alkylenediamines corresponding to the formula:

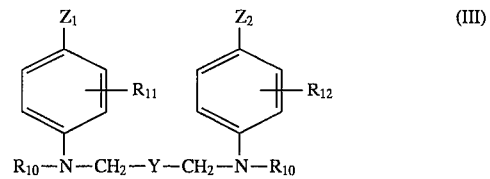

(III)

in which:

$Z_1$ and $Z_2$, which may be identical or different, represent hydroxyl groups or groups $NHR_3$, where $R_3$ denotes a hydrogen atom or a lower alkyl radical;

$R_{11}$ and $R_{12}$, which may be identical or different, represent either hydrogen atoms or halogen atoms or alternatively alkyl groups;

$R_{10}$ represents a hydrogen atom, an alkyl or hydroxyalkyl group or an aminoalkyl group in which the amino residue may be substituted;

Y represents a radical selected from the group consisting of the following radicals: —$(CH_2)_n$—, —$(CH_2)_m$—O—$(CH_2)_m$—, $(CH_2)_m$—CHOH—$(CH_2)_m$—,

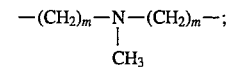

n being an integer between 0 and 8 and m an integer between 0 and 4, it being possible for this base to take the form of its addition salts with acids.

The alkyl or alkoxy radicals preferably denote a group having 1 to 4 carbon atoms, and in particular methyl, ethyl, propyl, methoxy or ethoxy.

Among the compounds of formula (III), there may be mentioned N,N'-bis (β-hydroxyethyl) -N,N'-bis (4-aminophenyl)-1,3-diamino-2-propanol, N,N'-bis (β2 -hydroxyethyl) N,N'-bis(4-aminophenyl)ethylenediamine, N,N'-bis(4-aminophenyl)tetramethylenediamine, N,N'-bis (β-hydroxyethyl) N,N'-bis (4-aminophenyl)tetramethylenediamine, N,N'-bis(4-methylaminophenyl)tetramethylenediamine and N,N'-bis-(ethyl) -N,N'-bis(4-amino-3-methylphenyl)ethyl enediamine.

The meta-phenylenediamines which can be used in the invention correspond to the formula (IV):

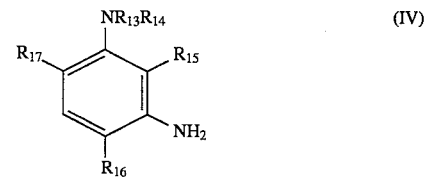

(IV)

in which:

$R_{13}$ and $R_{14}$ denote, independently of one another, hydrogen or a $C_1$-$C_4$ alkyl or $C_1$-$C_4$ hydroxyalkyl group;

$R_{15}$ denotes hydrogen or a $C_1$-$C_4$ alkyl or alkoxy group;

$R_{16}$ denotes a hydrogen atom or a $C_1$-$C_4$ alkyl or $C_1$-$C_4$ hydroxyalkoxy or $C_1$-$C_4$ alkoxy group;

$R_{17}$ denotes a hydrogen atom or a $C_1$-$C_4$ alkyl, $C_1$-$C_4$ alkoxy, $C_1$-$C_{14}$ hydroxyalkyl, $C_1$-$C_4$ hydroxyalkoxy or $C_1$-$C_4$ polyhydroxyalkoxy group, a halogen atom or a carbon ($C_1$-$C_4$ alkoxy) , 2,4-diaminophenoxy ($C_1$-$C_4$ alkoxy) or $C_1$-$C_4$ amino-alkoxy group;

with the proviso that, if $R_{17}$ denotes carboxyalkoxy or 2,4-diaminophenoxalkoxy, then $R_{13}$, $R_{14}$, $R_{15}$ and $R_{16}$ denote hydrogen.

These compounds can be used in free or salified form.

More especially preferred meta-phenylenediamines corresponding to the formula (IV) are chosen from 1,3-diaminobenzene, 1-methoxy-2,4-diaminobenzene, 1-(2-hydroxyethyloxy) -2,4-diaminobenzene, 1-ethoxy-2,4-diaminobenzene, 1-methyl-2,6-diaminobenzene, 1-amino-3- [N,N-bis-(2-hydroxyethyl) amino]benzene, 1-(β-hydroxyethyl)-2,4-diaminobenzene, 1-methoxy-2-amino-4-(β-hydroxyethylamino) benzene, 1,3-diamino-4-(β-aminoethyloxy) benzene, 1-(2-hydroxyethyloxy)-2-amino-4-(methylamino)benzene, 2,4-diaminophenoxyacetic acid, 4,6-bis (2-hydroxyethyloxy) -1,3-diaminobenzene, 2,4-diamino -5-methylphenetole, 2,4-diamino-5-(β-hydroxyethyloxy)toluene and 2,4-dimethoxy-1,3-diaminobenzene.

The dyeing compositions for keratinous fibres, especially for human hair, which constitute another subject of the invention, are essentially characterized in that they contain, in a cosmetically acceptable medium suitable for the dyeing of keratinous fibres, this medium being cosmetic when the compositions are applied to human hair, containing at least one para and/or ortho oxidation dye precursor, at least one meta-phenylenediamine and at least one benzimidazole derivative corresponding to the formula (I).

The more especially preferred compounds used in the compositions according to the invention are those defined above.

An especially preferred embodiment consists in using, in the same composition, the benzimidazole derivative of the formula (I), at least one metaphenylenediamine defined above, at least one paraphenylenediamine and at least one double base of the bis(phenyl)alkylenediamine family.

According to the invention, the compositions can also contain other couplers customarily used in dyeing compositions for keratinous fibres, especially for hair, such as, more especially, meta-diphenols, meta-aminophenols, meta-acylaminophenols, meta-ureidophenols, meta-carbalkoxyaminophenols, hydroxynaphthols, couplers possessing an active methylene group, such as β-keto compounds, pyrazolones or the indole couplers described, more especially, in the Patent Applications and Patents FR-A-2,636, 236, EP-A-0,428,442, EP-A-0,428,441, EP-A-0,496,653 and EP-A-0,424,261, as well as 4-hydroxyindole.

Among the couplers, there may be mentioned, more especially, meta-aminophenol, 1,3-dihydroxy-4-chlorobenzene, 1,3-dihydroxybenzene, α-naphthol, 6-hydroxybenzomorpholine, 1-methyl-2-hydroxy-4-aminobenzene, 1-methyl-2-hydroxy-4-(2-hydroxyethyl)aminobenzene, 1,3-dihydroxy-2-methylbenzene, 1-hydroxy-3,4-methylenedioxybenzene, 1-(β-hydroxyethylamino)-3,4-methylenedioxybenzene, 2-bromo-4,5-methylenedioxyphenol, 2-amino-5-acetamidophenol, 2,6-diaminopyridine, 6-hydroxyindole, 7-hydroxyindole and 7-aminoindole.

It is possible to use, together with the oxidation dye precursors and the couplers mentioned above, direct dyes such as azo or anthraquinone dyes or nitro derivatives of the benzene series, in particular for the purpose of varying the hue or enriching with glints the colorations provided by the oxidation dye precursors.

The benzimidazole derivative of the formula (I) and the dyeing compositions defined above are employed together with an oxidizing agent, which can be introduced into the composition immediately before use or applied to the fibres before, during or after the application of the dyeing composition containing the precursors defined above.

As oxidizing agent, hydrogen peroxide, urea peroxide, alkali metal bromates and persalts such as perborates and persulphates may be mentioned more especially, hydrogen peroxide being more especially preferred.

Ready-for-use dyeing compositions constitute another subject of the invention, and are characterized in that they contain, in a medium suitable for dyeing:

a) at least one derivative of the benzimidazole family of formula (I), b) at least one para and/or ortho oxidation dye precursor chosen from para-phenylenediamines, paraaminophenols, heterocyclic precursors, ortho-aminophenols, ortho-phenylenediamines and so-called double bases of the bis(phenyl)alkylenediamine family, c) at least one meta-phenylenediamine, and d) at least one oxidizing agent defined above.

The para and/or ortho type oxidation dye precursors as well as the couplers may be introduced into the compositions according to the invention either in free base form or in the form of salts, such as in hydrochloride, hydrobromide or sulphate form.

The para and/or ortho type oxidation dye precursors together with the couplers used according to the invention collectively represent from 0.02 to 10%, and preferably from 0.1 to 10%, by weight relative to the total weight of the composition. The concentration of compounds of formula (I) is generally between 0.004 and 3.5%, and preferably between 0.05 and 3.5%, by weight relative to the total weight of the composition. The concentration of metaphenylenediamine is generally between 0.004 and 3.5%, and preferably between 0.01 and 3.5%, by weight relative to the total weight of the composition.

The ratio of the meta-phenylenediamine to the benzimidazole derivative is preferably between 0.01 and 6.5.

The pH of the compositions applied to the keratinous fibres, and especially hair, is generally between 3 and 11.

This pH is adjusted by the use of acidifying or alkalinizing agents which are well known in the hair dyeing field.

The dyeing compositions according to the invention generally contain anionic, cationic, nonionic or amphoteric surfactants or mixtures thereof which are well known in the prior art.

These surfactants are present in the compositions according to the invention in proportions of between 0.5 and 55% by weight, and preferably between 2 and 50% by weight, relative to the total weight of the composition.

These compositions can also contain organic solvents to solubilize compounds which might not be sufficiently soluble in water. Among these solvents, there may be mentioned, as an example, $C_1$–$C_4$ lower alkanols such as ethanol and isopropanol; glycerol; glycols or glycol ethers such as 2-butoxyethanol, ethylene glycol, propylene glycol and diethylene glycol monoethyl ether and monomethyl ether, as well as aromatic alcohols such as benzyl alcohol or phenoxyethanol and similar products or mixtures thereof.

The solvents are preferably present in proportions of between 1 and 40% by weight, and especially between 5 and 30% by weight, relative to the total weight of the composition.

The thickening agents which may be added to the compositions according to the invention may be chosen from sodium alginate, gum arabic, cellulose derivatives, acrylic acid polymers and xanthan gum. It is also possible to use inorganic thickening agents such as bentonire.

These thickening agents are preferably present in proportions of between 0.1 and 5%, and especially between 0.2 and 3%, by weight relative to the total weight of the composition.

The antioxidants which may be present in the compositions are chosen especially from sodium sulphite, thioglycolic acid, sodium bisulphite, dehydroascorbic acid, hydroquinone and homogentisic acid. These antioxidants are present in the composition in proportions of between 0.05 and 1.5% by weight relative to the total weight of the composition.

These compositions may also contain other cosmetically acceptable adjuvants such as, for example, penetrating agents, sequestering agents, perfumes, buffers, and the like.

The compositions according to the invention can assume various forms, such as the form of liquids, creams or gels, or any other form suitable for carrying out a dyeing of keratinous fibres, and in particular human hair. These compositions may be packaged in aerosol cans in the presence of a propellent agent.

According to the invention, the process consists in applying to the keratinous fibres a composition, prepared at the time of use, containing at least one coupler of formula (I), at least one meta-phenylenediamine, at least one para type oxidation dye precursor and at least one oxidizing agent in a sufficient amount to be able to develop a coloration.

A 20-volumes hydrogen peroxide solution is preferably used. The mixture obtained is applied to the hair and left in place for 10 to 40 minutes, and preferably 15 to 30 minutes, after which the hair is rinsed, washed with shampoo, rinsed again and dried.

Another embodiment consists in applying separately a composition (A) containing the benzimidazole coupler of formula (I), the meta-phenylenediamine and the oxidation dye precursor, and then, after rinsing, a composition (B) containing the oxidizing agent.

It is also possible, according to the invention, to apply separately a composition containing the oxidation dye precursor, and then, after rinsing, to apply a composition containing the benzimidazole coupler of formula (I), the meta-phenylenediamine and the oxidizing agent.

The conditions of exposure and of drying or washing are similar to those described above.

The examples which follow are intended to illustrate the invention, no limitation, however, being implied.

EXAMPLES 1 TO 3

Hair dyeing is carried out by applying to natural grey hair which is 90% white a (weight for weight) mixture, prepared at the time of use, of the dyeing composition (A) and the oxidizing composition (B).

This mixture is left to act for 30 minutes, and the hair is then rinsed and shampooed. After drying, the hair is dyed in the hue specified at the bottom of the table.

TABLE

| in g | 1 | 2 | 3 |
|---|---|---|---|
| Dyeing composition (A) | | | |
| 4-Hydroxybenzimidazole.HBr | 0.0047 | 1.08 | 0.3 |
| para-Phenylenediamine.2HCl | 0.0382 | 0.01 | 3.1 |
| 2,6-Dimethoxy-meta-phenylene-diamine.2HCl | 0.0063 | | |
| 4,6-Bis(β-hydroxyethyloxy)-meta-phenylenediamine.2HCl | | 1.806 | |
| 1-Amino-3-(β-hydroxyethyl-amino)-g-methoxybenzene, 2HCl | | | 0.423 |
| para-Toluenediamine.2HCl | | 0.92 | |
| Dyeing vehicle (I) | X | X | X |
| Water qs | 100 | 100 | 100 |
| Oxidizing composition (B) | | | |
| 20-volumes hydrogen peroxide solution | 100 | 100 | 100 |
| Phosphoric acid qs pH 3 | | | |
| Hues obtained: on natural grey hair, 90% white | light beige | intense blue | brown |

DYEING VEHICLE (I)

| | |
|---|---|
| Octyldodecanol sold under the name EUTANOL G by the company HENKEL | 8 g |
| Oleic acid | 20 g |
| Monoethanolamine lauryl sulphate sold at a concentration of 33% of AS under the name SIPON LM35 by the company HENKEL | 1 g AS |
| Ethyl alcohol | 10 g |
| Benzyl alcohol | 10 g |
| Oxyethylenated cetyl/stearyl alcohol containing 33 mol of ethylene oxide, sold under the name SIMULSOL GS by the company SEPPIC | 2.4 g |
| Cationic polymer in aqueous solution containing 60% of AS, described and prepared according to French Patent 2,270,846, consisting of recurring units of formula: $$\left[ \begin{array}{c} CH_3 \\ | \\ N^+ - (CH_2)_3 - N^+ - (CH_2)_6 \\ | \\ CH_3 \end{array} \begin{array}{c} CH_3 \\ | \\ \\ | \\ CH_3 \end{array} \right]$$ $Cl^-$  $Cl^-$ | 2.22 g AS |
| Monoethanolamine | 7.5 g |
| Linoleic acid diethanolamide sold under the name COMPERLAN F by the company HENKEL | 8 g |
| Ammonia solution, 20% | 10.2 g |
| Sodium metabisulphite in 35% aqueous solution | 0.46 g AS |
| Hydroquinone | 0.15 g |
| 1-Phenyl-3-methyl-5-pyrazolone | 0.2 g |
| Sequestering agent qs | |

EXAMPLES 4 AND 5

The following compositions are prepared:

TABLE

| in g | 4 | 5 |
|---|---|---|
| Dyeing composition (A) | | |
| 4-Hydroxybenzimidazole.HBr | 0.005 | 1.08 |
| para-Phenylenediamine.2HCl | 0.038 | 0.01 |
| para-Toluylenediamine.2HCl | | 0.92 |
| 2,4-Diaminophenoxyethanol | 0.006 | 1.46 |
| Dyeing vehicle (II) | X | X |
| Water qs | 100 | 100 |
| Oxidizing composition (B) | | |
| 20-volumes hydrogen peroxide solution (pH 3) | 100 | 100 |
| Hues obtained: | light blond | black |

DYEING VEHICLE (II)

| | |
|---|---|
| Polyglycerolated oleyl alcohol containing 2 mol of glycerol | 4 g |
| Polyglycerolated oleyl alcohol containing 4 mol of glycerol (78% of AS) | 5.69 g AS |
| Oleic acid | 3 g |
| Oleylamine containing 2 mol of ethylene oxide, sold under the name ETHOMEEN O12 by the company AKZO | 7 g |
| Diethylaminopropyl laurylaminosuccinamate sodium salt containing 55% of AS | 3 g AS |
| Oleyl alcohol | 5 g |
| Oleic acid diethanolamide | 12 g |

-continued

| DYEING VEHICLE (II) | |
|---|---|
| Propylene glycol | 3.5 g |
| Ethyl alcohol | 7 g |
| Dipropylene glycol | 0.5 g |
| Propylene glycol monomethyl ether | 9 g |
| Sodium metabisulphite in aqueous solution containing 35% of AS | 0.455 g AS |
| Ammonium acetate | 0.8 g |
| Antioxidant, sequestering agent qs | |
| Perfume, preservative qs | |
| Ammonia solution containing 20% of $NH_3$ | 10 g |

The composition obtained is mixed weight for weight with hydrogen peroxide assaying at 20 volumes. The mixture is applied to bleached hair on the basis of 28 g to 3 g of hair, for 30 minutes. The hair is then rinsed, washed with a standard shampoo and dried.

The hair coloration is evaluated visually.

We claim:

1. Dyeing composition for keratinous fibres, comprising, in a medium suitable for the dyeing of keratinous fibres, an effective amount of at least one para or ortho oxidation dye precursor or mixture thereof, an effective amount at least one meta-phenylenediamine and an effective amount of, as coupler, at least one benzimidazole derivative corresponding to the formula (I):

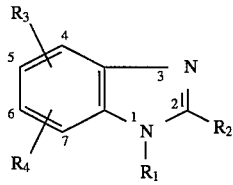

in which:

$R_1$ represents a hydrogen atom of a $C_1$–$C_4$ alkyl radical;

$R_2$ represents a hydrogen atom or a $C_1$–$C_4$ alkyl radical or a phenyl radical;

$R_3$ represents a hydroxyl, amino or methoxy radical;

$R_4$ represents a hydrogen atom or a hydroxyl or methoxy or $C_1$–$C_4$ alkyl radical;

with the proviso that:

when $R_3$ denotes $NH_2$, it occupies position 4;

when $R_3$ is at position 4, $R_4$ is at position 7; and when $R_3$ is at position 5, then $R_4$ is at position 6.

2. Composition according to claim 1, wherein the benzimidazole derivative is 4-hydroxybenzimidazole, 4-aminobenzimidazole, 4-hydroxy-7-methylbenzimidazole, 2-methyl-4-hydroxybenzimidazole, 1-butyl-4-hydroxybenzimidazole, 2-methyl-4-aminobenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole or 5,6-dimethoxybenzimidazole.

3. Composition according to claim 1, wherein the oxidation dye precursors are para-phenylenediamines, para-aminophenols, heterocyclic para precursors or bis(phenyl)alkylenediamines.

4. Composition according to claim 3 wherein the para-phenylenediamine is a compound of formula (II):

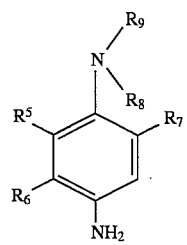

in which:

$R_5$, $R_6$ and $R_7$, which may be identical or different, represent a hydrogen or halogen atom, an alkyl or hydroxyalkyl radical having 1 to 4 carbon atoms, an alkoxy radical having 1 to 4 carbon atoms or a carboxyl or sulpho radical;

$R_8$ and $R_9$, which may be identical or different, represent a hydrogen atom or an alkyl, hydroxyalkyl, alkoxyalkyl, carbamoylalkyl, mesylaminoalkyl, acetylaminoalkyl, aminoalkyl, ureidoalkyl, carbalkoxyinoalkyl, sulphoalkyl, piperidinoalkyl or morpholinoalkyl radical, these alkyl or alkoxy groups having from 1 to 4 carbon atoms, or alternatively $R_8$ and $R_9$, together with the nitrogen atom to which they are linked, for a piperidino or mopholino heterocycle, with the proviso that $R_5$ or $R_7$ represents a hydrogen atom when $R_8$ and $R_9$ do not represent a hydrogen atom, or the salts of these compounds.

5. Composition according to claim 3 wherein the para-phenylenediamines are p-phenylenediamine, p-toluylenediamine, methoxy-para-phenylenediamine, chloro-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-di-propyl-para-phenylenediamine, 3-methyl-4-amino-N,N-diethylaniline, N,N-bis(β-hydroxyethyl)-para-phenylenediamine, 3-methl-4-amino-N,N-bis(β-hydroxyethyl)aniline, 3-chloro-4-amino-N,N-bis(β-hydroxyethyl)aniline, 4-amino-N-ethyl-N-(carbamoylmethyl)aniline, 3-methyl-4-amino-N-ethyl-N-(carbamoylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl) aniline, 4-amino-N-ethyl-N-(β-mesylaminoethyl)aniline, 3 -methyl-4-amino-N-ethyl-N-(β-mesylaminoethyl)aniline, 4-amino-N-ethyl-N-(β-sulphoethyl)aniline, 3-methyl -4-amino-N-ethyl-N-(β-sulphoethyl)aniline, N-(4-aminophenyl)morpholine, N-(4-aminophenyl)piperidine, 2-hydroxyethyl-para-phenylenediamine, fluoro-para-phenylenediamine, carboxy-para-phenylenediamine, sulpho-paraphenylenediamine, 2-isopropyl-para-phenylenediamine, 2-n-propyl-para-phenylenedlamine, hydroxy-2-n-propyl-para-phenylenediamine or 2 -hydroxymethyl-para-phenylenediamine.

6. Composition according to claim 3 wherein the p-aminophenols are p-aminophenol, 2-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl -4-aminophenol, 2-(β-hydroxyethyl)-4-aminophenol, 2-methoxy-4-aminophenol, 3-methoxy-4-aminophenol, 2,5-dimethyl-4- aminophenol, 2-methoxymethyl-4-aminophenol, 2-aminomethyl-4-aminophenol or 2-(β-hydroxyethylaminomethyl) -4-aminophenol.

7. Composition according to claim 1 wherein the ortho oxidation dye precursors are ortho-aminophenols or ortho-phenylenediamines.

8. Composition according to claim 3 wherein the bis(phenyl)alkylenediamines are compounds of the formula (III):

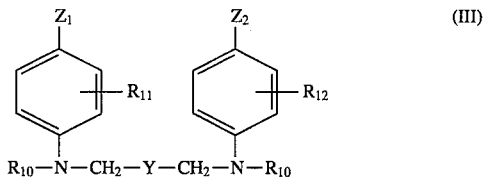

in which:

$Z_1$ and $Z_2$, which may be identical or different, represent hydroxyl groups or groups $NHR_3$, where $R_3$ denotes a hydrogen atom or a lower alkyl radical;

$R_{11}$ and $R_{12}$, which may be identical or different, represent either hydrogen atoms or halogen atoms or alternatively alkyl groups;

$R_{10}$ represents a hydrogen atom, an alkyl or hydroxyalkyl group or an aminoalkyl group in which the amino residue may be substituted;

Y represents a radical selected from the group consisting of the following radicals: $-(CH_2)_n-$, $-(CH_2)_m-O-(CH_2)_m-$, $(CH_2)_m-CHOH-(CH_2)_m-$,

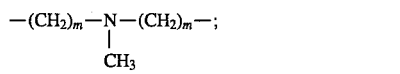

n being an integer between 0 and 8 and m an integer between 0 and 4, or the acid addition salts of these compounds.

9. Composition according to claim 5, wherein the bis(phenyl)alkylenediamines are N,N'-bis(β-hydroxyethyl) -N,N'-bis(4-aminophenyl)-1,3-di-amino-2-propanol, N,N'-bis(β-hydroxyethyl)-N,N'-bis-(4-aminophenyl)ethylenediamine, N,N'-bis(4-aminophenyl)tetramethylenediamine, N,N'-bis(β-hydroxyethyl)-N,N'-bis-(4-aminophenyl)tetramethylenediamine, N,N'-bis(4-methylaminophenyl) tetramethylenediammine or N,N'-bis(ethyl) N,N'-bis(4-amino-3-methylphenyl)ethylenediamine.

10. Composition according to any one of claim 1 wherein the meta-phenylenediamine is a compound corresponding to the formula:

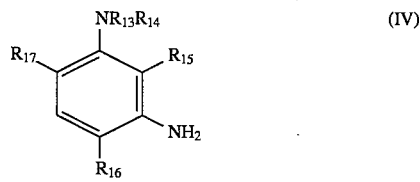

in which:

$R_{13}$ and $R_{14}$ denote, independently of one another, hydrogen or a $C_1$-$C_4$ alkyl or $C_1$-$C_4$ hydroxyalkyl group;

$R_{15}$ represents hydrogen or $C_1$-$C_4$ alkyl or alkoxy;

$R_{16}$ denotes a hydrogen atom or a $C_1$-$C_4$ alkyl or $C_1$-$C_4$ hydroxyalkoxy or $C_1$-$C_4$ alkoxy group;

$R_{17}$ represents a hydrogen atom or a $C_1$-$C_4$ alkyl, $C_1$-$C_4$ alkoxy, $C_1$-$C_4$ hydroxyalkyl, $C_1$-$C_4$ hydroxyalkoxy, $C_1$-$C_4$ polyhydroxyalkoxy, halogen, carboxy ($C_1$-$C_4$ alkoxy), 2,4 -diaminophenoxy($C_1$-$C_4$ alkoxy) or $C_1$-$C_4$ aminoalkoxy group;

with the proviso that, if $R_{17}$ denotes carboxy($C_1$-$C_4$ alkoxy) or 2,4-diaminophenoxy($C_1$-$C_4$ alkoxy), then $R_{13}$, $R_{14}$, $R_{15}$ and $R_{16}$ denote hydrogen.

11. Composition according to claim 10, wherein the meta-phenylenediamines are 1,3-diaminobenzene, 1-methoxy-2,4-diaminobenzene, 1- (2-hydroxyethyloxy)-2,4-diaminobenzene, 1-ethoxy2,4-diaminobenzene, 1-methyl-2,6-diaminobenzene, 1-amino-3- [N,N-bis (2-hydroxyethyl)amino]benzene, 1-(β-hydroxyethyl) -2,4-diaminobenzene, 1-methoxy-2-amino-4-(β-hydroxyethylamino)benzene, 1,3-diamino-4-(β-aminoethyloxy) benzene, 1-(2-hydroxyethyloxy)-2-amino-4-(methylamino) benzene, 2,4 -diaminophenoxyacetic acid, 4,6-bis (2-hydroxyethyloxy)-1,3-diaminobenzene, 2,4-diamino-5-methylphenetole, 2,4 -diamino-5-(β-hydroxyethyloxy) toluene or 2,4-dimethoxy-1,3-diaminobenzene.

12. Composition according to claim 1 wherein the composition it contains at least one benzimidazole derivative corresponding to the formula (I), at least one para-phenylenediamine, at least one meta-phenylenediamine and a bis(phenyl)alkylenediamine.

13. Composition according to claim 1 wherein the composition it also contains couplers other than meta-phenylenediamines and the benzimidazole derivatives of the formula (I), comprising metadiphenols, meta-aminophenols, meta-acylaminophenols, meta-ureidophenols, meta-carbalkoxyaminophenols, hydroxynaphthols, or couplers containing an active methylene group, chosen from β-keto derivatives, pyrazolones or indole couplers.

14. Composition according to claim 13, wherein the couplers other than the meta-phenylenediamine or the benzimidazole derivatives of formula (I) are meta-aminophenol, 1,3-dihydroxybenzene, 1,3-dihydroxy-4-chlorobenzene, α-naphthol, 6-hydroxybenzomorpholine, 1-methyl-2-hydroxy-4-aminobenzene, 1-methyl-2-hydroxy-4-(2-hydroxyethyl)aminobenzene, 1,3-dihydroxy-2-methylbenzene, 1-hydroxy-3,4-methylenedioxybenzene, 1-(β-hydroxyethylamino)-3,4-methylenedioxybenzene, 2-bromo- 4,5-methylenedioxyphenol, 2-amino-5-acetamidophenol, 2,6-diaminopyridine, 6-hydroxyindole, 7-hydroxyindole or 7-aminoindole.

15. Dyeing composition for keratinous fibres claim 1 further comprising an oxidizing agent in sufficient amounts to develop a coloration on the the treated fibres.

16. Composition according to claim 1 wherein the benzimidazole derivative of formula (I) is present in proportions of between 0.004 and 3.5% by weight relative to the total weight of the composition and wherein the metaphenylenediamines are present in proportions of between 0.004 and 3.5% by weight relative to the total weight of the composition.

17. Composition according to claim 13, wherein the para- or ortho-oxidation dye precursors, the metaphenylenediamines, the benzimidazole derivatives of formula (I) and the other couplers collectively are present in proportions ranging from 0.02 to 10% by weight relative to the total weight of the composition.

18. Process for dyeing keratinous fibres, comprising applying to the fibres an effective amount of at least one benzimidazole derivative of formula (I):

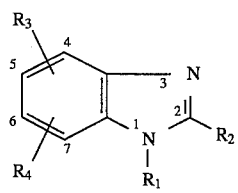 (I)

in which:

R₁ represents a hydrogen atom or a $C_1$–$C_4$ alkyl radical;

R₂ represents a hydrogen atom or a $C_1$–$C_4$ alkyl radical or a phenyl radical;

R₃ represents a hydroxyl, amino or methoxy radical;

R₄ represents a hydrogen atom or a hydroxyl or methoxy or $C_1$–$C_4$ alkyl radical;

with the proviso that:

when R₃ denotes $NH_2$, it occupies position 4;

when R₃ is at position 4, R₄ is at position 7; and when R₃ is at position 5, then R₄ is at position 6;

at least one para or ortho oxidation dye precursor or mixture thereof and at least one meta-phenylenediamine, each of these compounds being in a medium suitable for dyeing, and at least one oxidizing agent in sufficient amounts to develop a coloration of the fibres.

19. Process for dyeing keratinous fibres according to claim 18, wherein the at least one oxidizing agent is applied to the fibres before, during or after the remainder of the composition.

20. Dyeing composition for keratinous fibres, comprising, in a medium suitable for the dyeing of keratinous fibres, an effective amount of at least one para oxidation dye precursor selected from the group consisting of p-phenylenediamine, p-toluylenediamine, methoxy-para-phenylenediamine, chloro-paraphenylenediamine, 2,6-dimethyl-para-phenylenediamine, 2,6-diethyl-para-phenylenediamine, 2,5-dimethyl-para-phenylenediamine, N,N-bis(β-hydroxyethyl)-para-phenylenediamine, 4-amino-N-(β-methoxyethyl)aniline, 2-hydroxyethyl-para-phenylenediamine, fluoro-paraphenylenediamine, carboxy-para-phenylenediamine, sulpho-paraphenylenediamine, 2-isopropyl-para-phenylenediamine, 2-n-propyl-para-phenylenediamine, 2-hydroxymethyl-para-phenylenediamine, p-aminophenol, 2-methyl-4-aminophenol, 2-hydroxymethyl-4-aminophenol, 2-(β-hydroxyethyl)-4-aminophenol, 2-aminomethyl-4-aminophenol and 2-(β-hydroxyethylaminomethyl)-4-aminophenol, an effective amount of at least one meta-phenylenediamine selected from the group consisting of 1,3-diaminobenzene, 1-(2-hydroxyethyloxy)-2,4-diaminobenzene, 1-ethoxy-2,4-diaminobenzene, 1-methyl-2,6-diaminobenzene, 1-amino-3-[N,N-bis(2-hydroxyethyl)amino]benzene, 1-methoxy-2-amino-4-(β-hydroxyethylamino)benzene, 1-(2-hydroxy-ethyloxy)-2-amino-4-(methylamino)benzene, 2,4-diaminophenoxyacetic acid, 4,6-bis(2-hydroxyethyloxy)-1,3-diaminobenzene, 2,4-diamino-5-methylphenetole, 2,4-diamino-5-(β-hydroxyethyloxy)toluene and 2,4-dimethoxy-1,3-diaminobenzene and an effective amount of, as coupler, at least one benzimidazole derivative selected from the group consisting of 4-hydroxybenzimidazole, 4-aminobenzimidazole, 4-hydroxy-7-methylbenzimidazole, 2-methyl-4-hydroxybenzimidazole, 1-butyl-4-hydroxybenzimidazole, 2-methyl-4-aminobenzimidazole, 5,6dihydroxybenzimidazole, 5-hydroxy-6-methoxybenzimidazole, 4,7dihydroxybenzimidazole, 4,7-dihydroxy-1-methylbenzimidazole, 5,6-dihydroxy-1-methylbenzimidazole and 5,6-dihydroxy-2-methylbenzimidazole.

* * * * *